United States Patent
Govari et al.

(10) Patent No.: US 10,390,891 B2
(45) Date of Patent: Aug. 27, 2019

(54) HOLOGRAM LENS FOR POSITIONING AN ORTHOPEDIC IMPLANT

(71) Applicant: Biosense Webster (Israel) Ltd., Yokneam (IL)

(72) Inventors: Assaf Govari, Haifa (IL); Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 155 days.

(21) Appl. No.: 15/621,299

(22) Filed: Jun. 13, 2017

(65) Prior Publication Data

US 2018/0353304 A1 Dec. 13, 2018

(51) Int. Cl.
| | |
|---|---|
| A61F 2/46 | (2006.01) |
| A61B 17/72 | (2006.01) |
| G01B 7/00 | (2006.01) |
| A61B 34/20 | (2016.01) |
| A61B 17/17 | (2006.01) |

(Continued)

(52) U.S. Cl.
CPC .......... *A61B 34/20* (2016.02); *A61B 17/1707* (2013.01); *A61B 17/1725* (2013.01); *A61B 17/72* (2013.01); *A61B 90/361* (2016.02); *A61F 2/46* (2013.01); *G01B 7/003* (2013.01); *A61B 34/25* (2016.02); *A61B 2034/2051* (2016.02); *A61B 2090/365* (2016.02);
(Continued)

(58) Field of Classification Search
CPC ................................. A61B 34/20; A61F 2/46
See application file for complete search history.

(56) References Cited

U.S. PATENT DOCUMENTS

| | | |
|---|---|---|
| 5,391,199 A | 2/1995 | Ben Haim |
| 5,584,838 A | 12/1996 | Rona |

(Continued)

FOREIGN PATENT DOCUMENTS

| | | |
|---|---|---|
| EP | 1902679 A2 | 3/2008 |
| EP | 2096523 A1 | 9/2009 |

(Continued)

OTHER PUBLICATIONS

Londei, Roberto, et al., "Intra-operative augmented reality in distal locking", International Journal of Computer Assisted Radiology and Surgery, Springer, DE, vol. 10, No. 9, Mar. 27, 2015, pp. 1395-1403, ISSN: 1861-6410 (Abstract).

(Continued)

*Primary Examiner* — Christian A Sevilla
(74) *Attorney, Agent, or Firm* — Notaro, Michalos & Zaccaria P.C.

(57) ABSTRACT

An apparatus for positioning an orthopedic implant, the apparatus includes a magnetic receiver, a processor, and a personal display device. The magnetic receiver is configured to sense respective components of one or more magnetic fields generated by a field-generating device coupled to the orthopedic implant, and to produce corresponding electrical signals indicative of the sensed components of the one or more magnetic fields. The processor is configured to calculate, based on the electrical signals, a position of the orthopedic implant within an organ of a patient. The personal display device is configured to display at least part of the orthopedic implant overlaid on a scene, based on the position calculated by the processor.

12 Claims, 2 Drawing Sheets

(51) Int. Cl.
  *A61B 90/00* (2016.01)
  *G02B 27/01* (2006.01)
  *A61B 34/00* (2016.01)
  *A61B 90/50* (2016.01)

(52) U.S. Cl.
  CPC ... *A61B 2090/368* (2016.02); *A61B 2090/397* (2016.02); *A61B 2090/502* (2016.02); *G02B 27/017* (2013.01)

(56) References Cited

U.S. PATENT DOCUMENTS

| | | | |
|---|---|---|---|
| 6,239,724 | B1 | 5/2001 | Doron |
| 6,332,089 | B1 | 12/2001 | Acker |
| 6,484,118 | B1 | 11/2002 | Govari |
| 6,618,612 | B1 | 9/2003 | Acker |
| 6,690,963 | B2 | 2/2004 | Ben Haim |
| 9,649,160 | B2 * | 5/2017 | van der Walt ........ A61F 2/4657 |
| 2002/0065455 | A1 | 5/2002 | Ben Haim |
| 2003/0120150 | A1 | 6/2003 | Govari |
| 2004/0034355 | A1 | 2/2004 | Govari |
| 2004/0068178 | A1 | 4/2004 | Govari |
| 2006/0098851 | A1 | 5/2006 | Shoham |
| 2006/0173293 | A1 | 8/2006 | Marquart |
| 2008/0086145 | A1 | 4/2008 | Sherman |
| 2011/0019884 | A1 | 1/2011 | Blau |
| 2015/0374452 | A1 * | 12/2015 | Saito .................... A61B 90/36 600/424 |
| 2015/0375013 | A1 * | 12/2015 | Lachaine ............... A61B 8/085 600/439 |
| 2015/0379710 | A1 * | 12/2015 | Holsing ................. A61B 5/113 382/131 |
| 2016/0000414 | A1 * | 1/2016 | Brown ................... A61B 10/04 600/567 |
| 2017/0143443 | A1 * | 5/2017 | Tuma ..................... G09G 5/005 |
| 2017/0172668 | A1 * | 6/2017 | Aljuri .................... A61B 34/20 |

FOREIGN PATENT DOCUMENTS

| | | |
|---|---|---|
| WO | WO 96-05768 A1 | 2/1996 |
| WO | 2012/051512 A1 | 4/2012 |
| WO | 2012/109760 A1 | 8/2012 |
| WO | 2071/015738 A1 | 2/2017 |

OTHER PUBLICATIONS

Extended European Search Report for corresponding European patent application No. 18177186.6, dated Nov. 15, 2018.

* cited by examiner

HOLOGRAM LENS FOR POSITIONING AN ORTHOPEDIC IMPLANT

FIELD OF THE INVENTION

The present invention relates generally to medical devices, and particularly to methods and systems for positioning an orthopedic implant within a patient body.

BACKGROUND OF THE INVENTION

Orthopedic implants, such as intramedullary nails, are implanted in bone tissue of a patient. Various methods and systems are known in the art for tracking the position of an orthopedic implant inside the patient body.

For example, U.S. Patent Application Publication 2004/0034355 describes method and apparatus for distal targeting of locking screws in intramedullary nails. A sensor, such as a wireless sensor, having a plurality of field transponders, is disposed in an orthopedic appliance, such as an intramedullary nail. The sensor is capable of detecting and discriminating the strength and direction of the different fields generated by the field generators.

U.S. Patent Application Publication 2008/0086145 describes a system that enables targeting of an instrument placed within a drill bushing aligns the axis of a drill bushing with the axis of a transverse hole in an intramedullary nail. The system includes a probe having an elongated member with a distal end, a magnet that is polarized along its longitudinal axis that is mounted perpendicularly to the distal end of the elongated member; and a processor executing programmed instructions to determine a position and orientation of the magnetic sensor array with respect to the targeting magnet.

U.S. Pat. No. 5,584,838 describes a femoral nail which has a transverse hole, and an arrangement for generating a magnetic field which has a maximum strength along an axis of the transverse hole and which decreases in strength in directions radially away from the axis.

SUMMARY OF THE INVENTION

An embodiment of the present invention that is described herein provides an apparatus for positioning an orthopedic implant, the apparatus includes a magnetic receiver, a processor, and a personal display device. The magnetic receiver is configured to sense respective components of one or more magnetic fields generated by a field-generating device coupled to the orthopedic implant, and to produce corresponding electrical signals indicative of the sensed components of the one or more magnetic fields. The processor is configured to calculate, based on the electrical signals, a position of the orthopedic implant within an organ of a patient. The personal display device is configured to display at least part of the orthopedic implant overlaid on a scene, based on the position calculated by the processor.

In some embodiments, the scene includes at least the organ. In other embodiments, the personal display device is further configured to display an anatomical image of at least part of the organ, overlaid on the scene. In yet other embodiments, the orthopedic implant includes an opening, and the personal display device is configured to display a marker, indicative of the position of the opening, overlaid on the organ.

In an embodiment, the scene includes a hole formed in the organ, and the personal display device is configured to display an indication of whether the hole in the organ and the opening in the orthopedic implant are aligned with one another. In another embodiment, the displayed at least part of the orthopedic implant includes a three-dimensional (3D) hologram of the at least part of the orthopedic implant. In yet another embodiment, the scene includes the organ, and the personal display device is configured to render at least part of the organ partially transparent.

There is additionally provided, in accordance with an embodiment of the present invention, a method for positioning an orthopedic implant, the method includes sensing respective components of one or more magnetic fields generated by a field-generating device coupled to the orthopedic implant. Electrical signals indicative of the sensed components of the one or more magnetic fields are produced. Based on the electrical signals, a position of the orthopedic implant is calculated within an organ of a patient. Based on the calculated position, at least part of the orthopedic implant is displayed, on a personal display device, overlaid on a scene.

The present invention will be more fully understood from the following detailed description of the embodiments thereof, taken together with the drawings in which:

DETAILED DESCRIPTION OF EMBODIMENTS

Overview

Orthopedic implants, such as an intramedullary nail, are typically fixed to a receiving bone by drilling one or more holes into the bone, and fitting fixing apparatus, such as orthopedic locking screws, through the drilled holes and designated openings in the nail. A physician may apply anatomical imaging techniques, such as fluoroscopy, to align the designated openings with the drilled holes. However, it is highly desirable to reduce the amount of radiation in such procedures.

Embodiments of the present invention that are described hereinbelow provide improved techniques for aligning a designated opening in an orthopedic implant with a hole drilled by the physician in a receiving bone. In some embodiments, the physician applies a positioning apparatus for aligning the position and orientation of the opening with the drilled hole.

In some embodiments, the positioning apparatus comprises a magnetic receiver, which is configured to sense components of a triple-axis magnetic field generated by a field-generating device coupled to the orthopedic implant.

In some embodiments, the magnetic receiver comprises one or more magnetic position sensors, which are configured to sense components of the triple-axis magnetic field and to transmit, to a processor, respective signals indicative of the position of the field-generator within the receiving bone. In some embodiments, the magnetic receiver is further configured to produce electrical signals indicative of the sensed components of the magnetic field.

In some embodiments, the positioning apparatus comprises a processor, which is configured to calculate, based on the electrical signals, a position of the orthopedic implant within the receiving bone. In some embodiments, the positioning apparatus further comprises personal display goggles, which are configured to display, based on the position calculated by the processor, a three-dimensional (3D) hologram of the orthopedic implant overlaid on the bone.

In some embodiments, the positioning apparatus enables navigating the orthopedic implant to the target position within the bone, and aligning the position and orientation of the opening with the drilled hole.

The disclosed techniques enable fixing an implant to a receiving bone without exposing the patient and physician to hazardous X-ray radiation. These techniques enable reducing the cost and complexity of orthopedic implants, shortening the cycle time of orthopedic implanting procedures, and improving the safety of the patient and physician.

System Description

Figure 1:
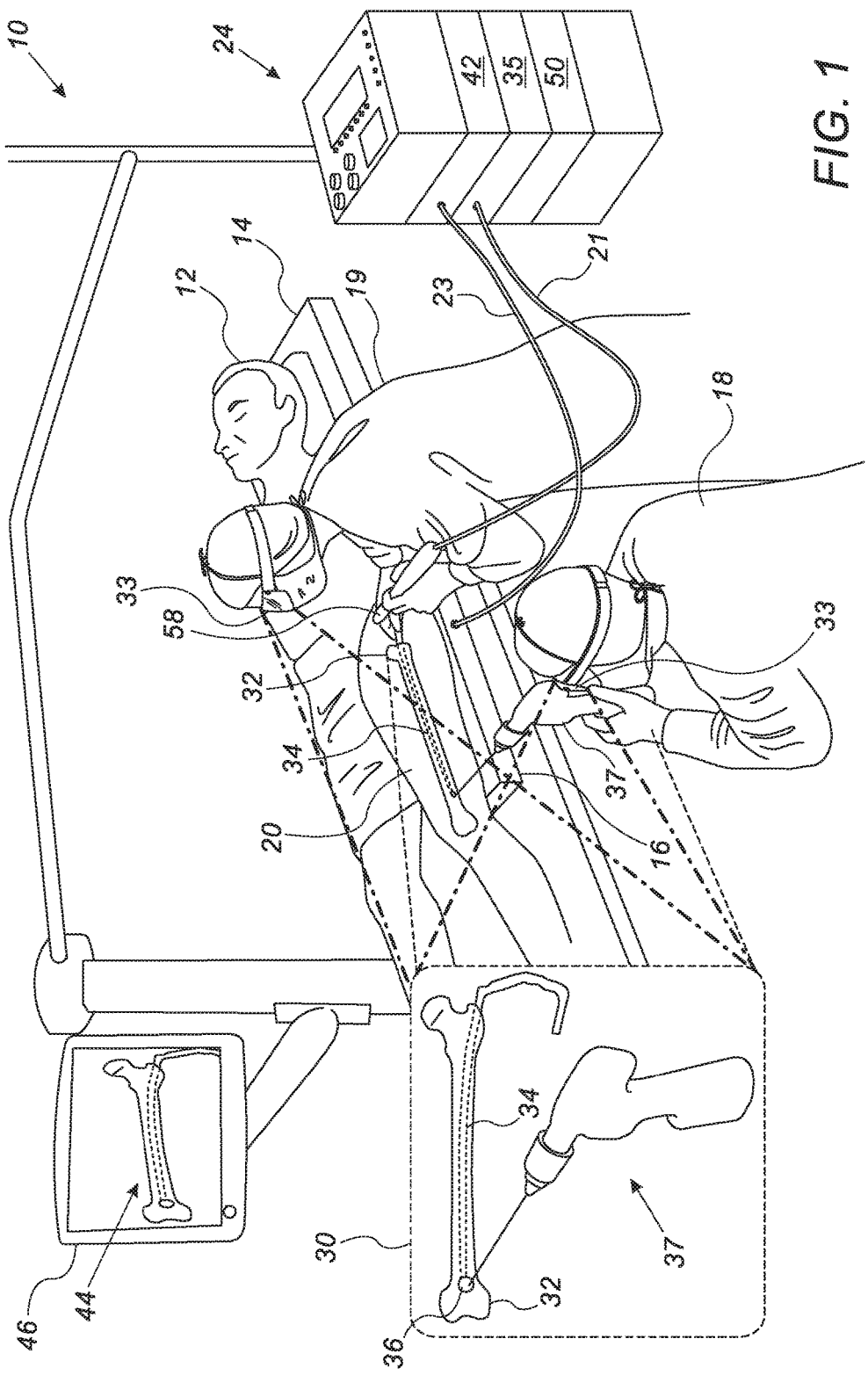
FIG. 1 is a schematic, pictorial illustration of an orthopedic procedure applying a system for implanting an orthopedic implant in a patient bone, in accordance with an embodiment of the present invention.

FIG. 1 is a schematic, pictorial illustration of an orthopedic procedure using system 10 for implanting an orthopedic implant 34 in a thigh 20 of a patient 12, in accordance with an embodiment of the present invention. In the example of FIG. 1, physicians 18 and 19 are implanting orthopedic implant 34 in a receiving bone 32 (e.g., a thigh bone) of patient 12 lying on an operating table 14. In the present context, the terms "patient" and "implantee" are used interchangeably, and refer to a recipient of implant 34.

In some embodiments, system 10 comprises a magnetic position tracking system comprising field-generators (shown in FIG. 2), a magnetic receiver 16 located below thigh 20 and/or within a wand 58, and additional components that will be described in detail below.

In some embodiments, wand 58 further comprises an industrial, scientific and medical (ISM) radiator, depicted in detail in FIG. 2 below.

In some embodiments, system 10 comprises an operating console 24, which comprises a processor 42, typically a general-purpose computer, with suitable front end and interface circuits for receiving signals from multiple sources of system 10, and for controlling the other components of system 20 described herein.

In some embodiments, magnetic receiver 16 comprises one or more magnetic position sensors, configured to sense magnetic fields, and connected to the interface circuitry in processor 42 via a cable 23. Processor 42 may be programmed in software to carry out the functions that are used by the system, and the processor stores data for the software in a memory 50. The software may be downloaded to console 24 in electronic form, over a network, for example, or it may be provided on non-transitory tangible media, such as optical, magnetic or electronic memory media. Alternatively, some or all of the functions of processor 42 may be carried out by dedicated or programmable digital hardware components.

In some embodiments, physician 18 drills a hole through the skin, flesh and bone 32 of thigh 20, using a drilling tool 37, or any other suitable technique.

In the exemplary procedure depicted in FIG. 1, physician 19 navigates implant 34 to a target position within bone 32, in which the drilled hole in bone 32 is aligned with a designated opening 36 of implant 34. Subsequently, physician 18 fixes implant 34 to bone 32 by fitting a fixing apparatus (not shown), such as an orthopedic locking screw, into the aligned hole of bone 32 and opening 36 of implant 34.

In some embodiments, console 24 comprises a driver circuit 35 that is configured to drive, via a cable 21, the ISM radiator of wand 58, operated by physician 19 or by any other operator. The ISM radiator and field-generator (shown in FIG. 2) are described in detail in FIG. 2 below.

In some embodiments, processor 42 is configured to calculate and display, on a user display 46, the position and orientation of orthopedic implant 34 overlaid (e.g., as a marker) on a pre-acquired anatomical image 44 of bone 32.

This method of position sensing is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Using Augmented Reality Goggles for Positioning an Orthopedic Implant

In some embodiments, system 10 comprises one or more personal displays, such as goggles 33, worn by at least one of physicians 18 and 19. In some embodiments, each goggles 33 comprise one or more displays (not shown) that may be coupled to a frame (not shown), for positioning against one or more eyes of each respective physician 18 and 19. In other embodiments, any other suitable configuration of goggles 33 may be applied.

In some embodiments, goggles 33 may be any suitable off-the-shelf augmented reality (AR) goggles, such as HoloLens™ produced by Microsoft Corporation (Redmond, Wash.), or Meta 2 produced by Meta company (San Mateo, Calif.).

In some embodiments, processor 42 is configured to store one or more pre-acquired images of orthopedic implant 34, and to convert the pre-acquired images into display signals of a three-dimensional hologram of at least part of orthopedic implant 34.

In some embodiments, goggles 33 are configured to exchange the display signals with processor 42, so as to display the hologram overlaid on a scene viewed by physicians 18 and 19.

Reference is now made to an inset 30. During the medical procedure, the gaze of physicians 18 and 19 is directed on a distant scene, such as on thigh 20 of patient 12. In an embodiment, each of physicians 18 and 19 is wearing goggles 33, which display the hologram of orthopedic implant 34, overlaid on bone 32. Note that typically, internal tissue of thigh 20, such as bone 32, are covered by skin and therefore, are invisible to physicians 18 and 19. In an embodiment, goggles 33 are further configured to display an anatomical image of at least part of these internal tissue, overlaid on thigh 20.

In this embodiment, bone 32 and the flesh and skin of thigh 20 are rendered partially transparent in goggles 33, so as to enable the display of implant 34. Note that the position of implant 34 is calculated by processor 42 and its hologram is displayed at the calculated position.

The fixation of implant 34 in bone 32 may be carried out in any suitable sequence. In an embodiment, physician 19 may navigate opening 36 of implant 34 to a target position within bone 32. Subsequently, physician 18 may direct drilling tool 37 to the position of opening 36 marked on bone 32, so as to drill the hole in bone 32.

In another embodiment, physicians 18 may drill the hole in bone 32 before inserting implant 34 therein. Then, physician 19 may apply goggles 33 to navigate opening 36 of implant 34, to the location of the drilled hole, and aligns opening 36 with the drilled hole in bone 32. Subsequently, physician 18 may fit the orthopedic locking screw (or any other suitable fixing apparatus), into the aligned hole of bone 32 and opening 36 of implant 34.

In some embodiments, goggles 33 are further configured to display on bone 32 (and/or on display 46), any suitable overlaid information, such as a marker indicating the position of opening 36.

Figure 2:
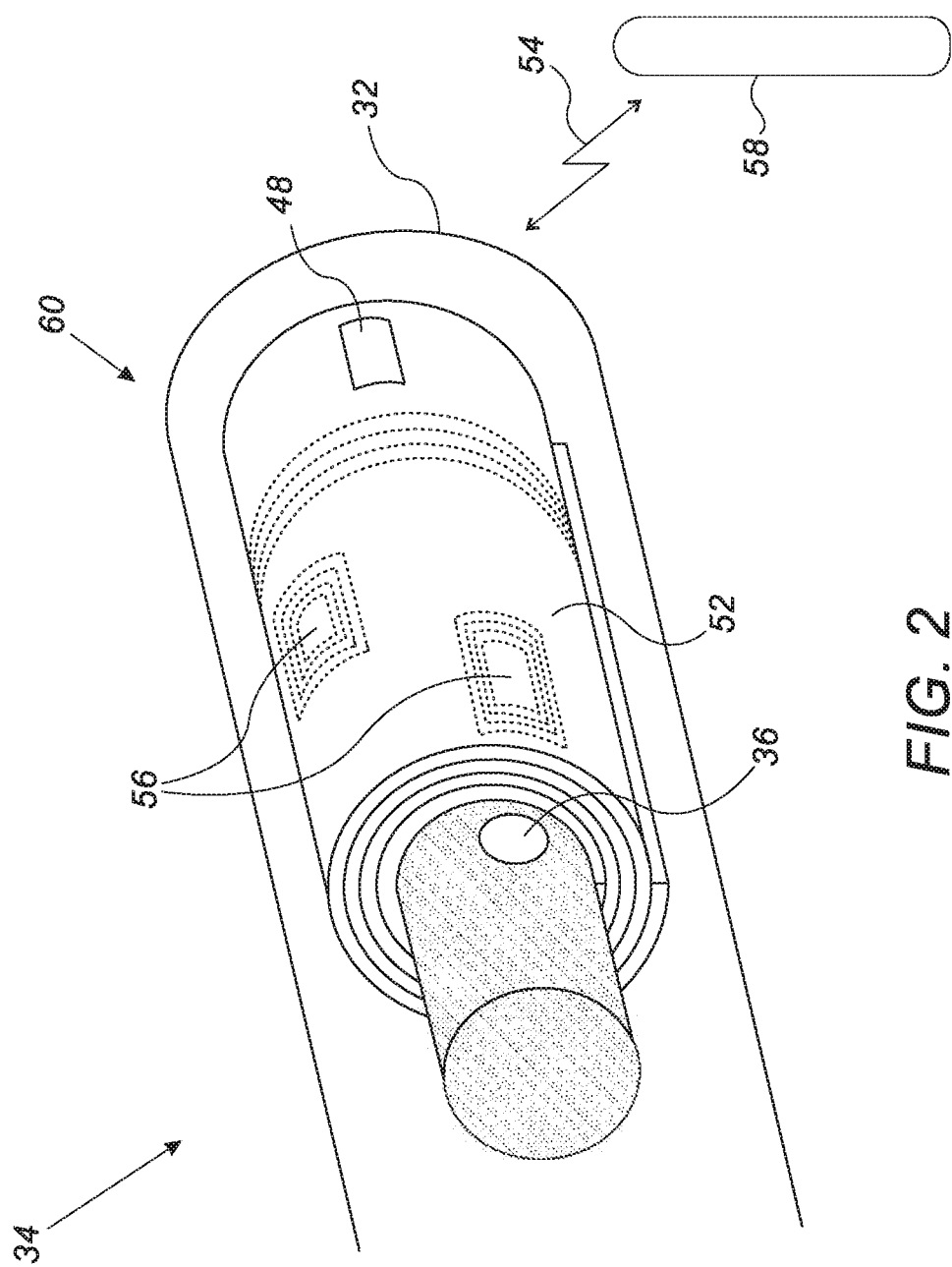
FIG. 2 is a schematic, pictorial illustration of a field-generator used for tracking and positioning an orthopedic implant in a patient bone, in accordance with an embodiment of the present invention.

Navigating an Orthopedic Implant in a Receiving Bone Using a Wireless Positioning Tool FIG. 2 is a schematic, pictorial illustration of a field-generator 60 used for setting the position and orientation of orthopedic implant 34 in bone 32, in accordance with an embodiment of the present invention.

In some embodiments, field-generator 60 comprises a flexible substrate, rolled around implant 34 at a predefined location relative to opening 36.

In some embodiments, the flexible substrate comprises a flexible circuit board 52 made from Kapton™ or any other suitable material. In some embodiments, one or more coils (typically three), such as coils 56, are formed on a single layer, or within multiple (e.g., three) respective layers of board 52. Coils 56 are made from a conductive material, such as copper, and are formed on board 52 using any suitable production technique.

In this configuration, each coil 56 has an axis orthogonal to the surface of board 52. In some embodiments, the axes of coils 56 are typically orthogonal to one another, but can be oriented relative to one another at any other suitable angle different from zero. In other words, the axes of coils 56 are not parallel to one another.

In some embodiments, three coils 56 of field-generator 60, are configured to apply to bone 32 a triple-axis magnetic field in the directions of the respective axes. The magnetic field is detected by the magnetic position sensors of receiver 16 and signals indicative of the position of field-generator 60 are transmitted to processor 42 via cable 23.

In alternative embodiments, the magnetic field is detected by the magnetic receiver of wand 58, and signals indicative of the position of field-generator 60 are transmitted to processor 42 via cable 21 and circuitry 35.

In these embodiments, the magnetic receiver of wand 58 may replace magnetic receiver 16, and circuitry 35 may further comprise a processor (not shown) that may replace processor 42.

In some embodiments, circuitry 48, which is mounted on board 52, is configured to harvest electrical power from electromagnetic (EM) energy 54 transmitted by the ISM radiator of wand 58. In some embodiments, the EM energy comprises an unlicensed ISM band power frequency, such as 13.56 MHz.

In some embodiments, circuitry 48 comprises a signal-generator, which is configured to generate three different alternate current (AC) signals at three different respective frequencies. Circuitry 48 is electrically connected to coils 56 so that each AC signal is used for driving a respective coil 56.

In other embodiments, field-generator 60 may comprise, instead of circuitry 48, any suitable power source configured to generate the AC signals.

In some embodiments the power source my apply energy harvesting techniques. For example, a device comprising one or more piezoelectric elements may be applied for harvesting energy from ambient temperature, vibration or flow of fluids within thigh 20.

In alternative embodiments, an implantable battery may be used instead of circuitry 48, for supplying the AC signals to coils 56. In these embodiments, the battery is electrically connected to coils 56, and located at any suitable position relative to implant 34. In these embodiments, the battery may be mounted on board 52, or positioned at any other suitable location internally or externally to orthopedic implant 34.

In some embodiments, field-generator 60 is sealed from tissue (e.g., bone 32) of patient 12, using an inert biocompatible sleeve made from Teflon™ or by using any other suitable sealing technique.

In some embodiments, physician 19 inserts implant 34, having field-generator 60 coupled thereto, into bone 32 and holds wand 58 in close proximity to circuitry 48 so as to transmit energy 54 thereto. Circuitry 48 converts energy 54 to AC signals driving coils 56, which produce the triple-axis magnetic field. In an embodiment, the magnetic receiver of wand 58 (and/or magnetic receiver 16) senses the magnetic field applied by coils 56, and transmits signals indicative of the position and orientation of field-generator 60 to processor 42.

In an embodiment, processor 42 estimates the position and orientation of opening 36 within bone 32 using the received signals indicating the position of field-generator 60 and respective predefined offset of each coil 56 relative to opening 36. In this embodiment, processor 42 tracks the position and orientation of opening 36 and displays the hologram of implant 34 overlaid on bone 32. In another embodiment, processor 42 displays a marker indicative of the position and orientation of opening 36 overlaid on image 44 and/or on bone 32.

In an embodiment, based on the position and orientation of the marker, physician 19 navigates implant 34 within bone 32 to a target position, in which the drilled hole of bone 32 is aligned with opening 36 of implant 34. Subsequently, fixes implant 34 to bone 32 by fitting the fixing apparatus into the hole of bone 32 and opening 36 of implant 34.

In alternative embodiments, field-generator 60 may comprise any suitable number of coils, having any suitable shape and arranged so that board 52 may be folded into any suitable shape, thereby arranging the axes of coils 56 at any suitable angle, which is typically not parallel with one another.

In these embodiments, the signal-generator of circuitry 48 is configured to generate any suitable number of AC signals for driving a respective number of coils. Furthermore, the flexibility of board 52 enables coupling field-generator 60 to any arbitrary-shaped three-dimensional (3D) implant, not limited to any specific shape.

In some embodiments, implant 34 refers to any type of orthopedic implant, such as a nail, a pin, a plate and a prosthesis, implanted in a limb or spine or any other bone tissue of patient 12.

The specific configurations shown in FIGS. 1 and 2 are simplified for the sake of clarity and are depicted purely by way of example. In alternative embodiments, system 10 may comprise any other suitable positioning and or position tracking apparatus, and those having ordinary skill in the art will be able to adapt the description, mutatis mutandis, for other types of medical systems. Furthermore, the configuration of field-generator 60 is depicted purely by way of example, any other suitable configuration may be applied for producing the fields described above.

In alternative embodiments, system 10 may comprise a positioning tool configured to apply one or more magnetic fields externally to the patient body, and to sense the applied magnetic fields using one or more sensors coupled to implant 34. For example, magnetic receiver 16 is replaced with a location pad, comprising field-generators, which is configured to generate a triple-axis magnetic field. In these embodiments, circuit board 52 and coils 56 may be applied as a triple-axis sensor, configured to sense the applied triple-axis magnetic field.

In an embodiment, the triple-axis sensor is further configured to transmit electrical signals indicative of the position of implant 34, to processor 42. The electrical signals may be transmitted wirelessly, using any suitable technique, such as radio-frequency (RF), or Bluetooth low energy (BLE).

Although the embodiments described herein mainly address orthopedic implants, the methods and systems described herein can also be used in other applications, such as in a breast implant expender having an implantable port, a gastric band port, and an implantable reservoir of an insulin pump.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus for positioning an orthopedic implant, the apparatus comprising:
    a magnetic receiver, which is configured to sense respective components of one or more magnetic fields generated by a field-generating device coupled to the orthopedic implant, and to produce corresponding electrical signals indicative of the sensed components of the one or more magnetic fields;
    a processor, which is configured to calculate, based on the electrical signals, a position of the orthopedic implant within an organ of a patient; and
    a personal display device, which is configured to display at least part of the orthopedic implant overlaid on a scene, based on the position calculated by the processor, wherein the displayed at least part of the orthopedic implant comprises a three-dimensional (3D) hologram of the at least part of the orthopedic implant.

2. The apparatus according to claim 1, wherein the scene comprises at least the organ.

3. The apparatus according to claim 1, wherein the personal display device is further configured to display an anatomical image of at least part of the organ, overlaid on the scene.

4. The apparatus according to claim 1, wherein the orthopedic implant comprises an opening, and wherein the personal display device is configured to display a marker, indicative of the position of the opening, overlaid on the organ.

5. The apparatus according to claim 4, wherein the scene comprises a hole formed in the organ, and wherein the personal display device is configured to display an indication of whether the hole in the organ and the opening in the orthopedic implant are aligned with one another.

6. The apparatus according to claim 1, wherein the scene comprises the organ, and wherein the personal display device is configured to render at least part of the organ partially transparent.

7. A method for positioning an orthopedic implant, the method comprising:
    sensing respective components of one or more magnetic fields generated by a field-generating device coupled to the orthopedic implant, and producing corresponding electrical signals indicative of the sensed components of the one or more magnetic fields;
    calculating, based on the electrical signals, a position of the orthopedic implant within an organ of a patient; and
    displaying, on a personal display device, at least part of the orthopedic implant overlaid on a scene, based on the calculated position, where displaying the at least part of the orthopedic implant comprises displaying a three-dimensional (3D) hologram of the at least part of the orthopedic implant.

8. The method according to claim 7, wherein the scene comprises at least the organ.

9. The method according to claim 7, wherein displaying on the personal display further comprises displaying an anatomical image of at least part of the organ, overlaid on the scene.

10. The method according to claim 7, wherein the orthopedic implant comprises an opening, and wherein displaying on the personal display comprises, displaying a marker, indicative of the position of the opening, overlaid on the organ.

11. The method according to claim 10, wherein the scene comprises a hole formed in the organ, and wherein displaying on the personal display device comprises displaying an indication of whether the hole in the organ and the opening in the orthopedic implant are aligned with one another.

12. The method according to claim 7, wherein the scene comprises the organ, and wherein displaying on the personal display device comprises rendering at least part of the organ partially transparent.

* * * * *